(12) United States Patent
Wenchell et al.

(10) Patent No.: US 8,746,531 B2
(45) Date of Patent: Jun. 10, 2014

(54) SURGICAL STAPLER

(71) Applicant: Covidien LP, Mansfield, MA (US)

(72) Inventors: Thomas Wenchell, Durham, CT (US); Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/769,961

(22) Filed: Feb. 19, 2013

(65) Prior Publication Data
US 2013/0186930 A1 Jul. 25, 2013

Related U.S. Application Data

(66) Division of application No. 12/637,841, filed on Dec. 15, 2009, now Pat. No. 8,408,441, Substitute for application No. 61/142,660, filed on Jan. 6, 2009.

(51) Int. Cl.
*A61B 17/04* (2006.01)
(52) U.S. Cl.
USPC .................. 227/175.1; 606/139; 606/219
(58) Field of Classification Search
CPC ............ A61B 17/115; A61B 17/1155; A61B 17/1114; A61B 17/068; A61B 2017/07214; A61B 17/1142; A61B 17/11; A61B 17/06166; A61B 2018/005; A61B 17/0469; A61B 17/064
USPC .............. 173/19, 175.1, 179.1; 606/139, 219; 227/19, 175.1, 175.2, 175.3, 179.1
See application file for complete search history.

(56) References Cited

U.S. PATENT DOCUMENTS

| 4,592,354 | A | | 6/1986 | Rothfuss |
|---|---|---|---|---|
| 4,665,917 | A | | 5/1987 | Clanton et al. |
| 4,703,887 | A | | 11/1987 | Clanton et al. |
| 5,261,920 | A | | 11/1993 | Main et al. |
| 5,309,927 | A | * | 5/1994 | Welch ............................ 128/898 |
| 5,350,104 | A | | 9/1994 | Main et al. |
| 5,445,644 | A | * | 8/1995 | Pietrafitta et al. ............. 606/151 |
| 6,053,390 | A | * | 4/2000 | Green et al. ................ 227/179.1 |
| 6,083,241 | A | | 7/2000 | Longo et al. |
| 6,959,851 | B2 | | 11/2005 | Heinrich |
| 7,128,748 | B2 | | 10/2006 | Mooradian et al. |
| 7,168,604 | B2 | * | 1/2007 | Milliman et al. .......... 227/176.1 |
| 7,399,305 | B2 | | 7/2008 | Csiky et al. |
| 7,776,060 | B2 | | 8/2010 | Mooradian et al. |
| 7,845,536 | B2 | | 12/2010 | Viola et al. |
| 7,922,743 | B2 | | 4/2011 | Heinrich et al. |
| 8,181,838 | B2 | * | 5/2012 | Milliman et al. .......... 227/175.1 |
| 8,181,840 | B2 | | 5/2012 | Milliman |
| 8,231,042 | B2 | * | 7/2012 | Hessler et al. ............. 227/179.1 |
| 8,236,015 | B2 | * | 8/2012 | Bettuchi et al. ................ 606/153 |

(Continued)

FOREIGN PATENT DOCUMENTS

| EP | 0594436 | 10/1993 |
|---|---|---|
| SU | 1509052 | 1/1988 |
| WO | WO87/06448 | 11/1987 |
| WO | WO2008/107918 | 9/2008 |

*Primary Examiner* — Stephen F Gerrity
*Assistant Examiner* — Eyamindae Jallow

(57) ABSTRACT

An anvil assembly comprising an anvil shaft and an anvil head, the anvil head having anvil depressions for farming surgical staples. The anvil head is mounted to the anvil shaft and the anvil shaft has a longitudinal axis and first and second spaced apart elongated projections attached to the anvil shaft and extending therefrom. The projections are configured and dimensioned to retain a purse string suture.

17 Claims, 10 Drawing Sheets

(56) References Cited

U.S. PATENT DOCUMENTS

| | | | |
|---|---|---|---|
| 8,272,555 B2 | 9/2012 | Rebuffat et al. | |
| 8,276,802 B2 | 10/2012 | Kostrzewski | |
| 8,281,974 B2* | 10/2012 | Hessler et al. | 227/179.1 |
| 8,312,885 B2* | 11/2012 | Bettuchi et al. | 128/898 |
| 8,343,185 B2* | 1/2013 | Milliman et al. | 606/219 |
| 8,360,295 B2* | 1/2013 | Milliman et al. | 227/175.1 |
| 8,418,909 B2 | 4/2013 | Kostrzewski | |
| 8,424,535 B2* | 4/2013 | Hessler et al. | 128/898 |
| 2003/0183671 A1* | 10/2003 | Mooradian et al. | 227/175.1 |
| 2005/0059997 A1 | 3/2005 | Bauman et al. | |
| 2006/0011698 A1 | 1/2006 | Okada et al. | |
| 2006/0085034 A1* | 4/2006 | Bettuchi | 606/219 |
| 2006/0108393 A1* | 5/2006 | Heinrich et al. | 227/179.1 |
| 2007/0203510 A1* | 8/2007 | Bettuchi | 606/153 |
| 2008/0210739 A1 | 9/2008 | Milliman et al. | |
| 2010/0213239 A1* | 8/2010 | Rebuffat et al. | 227/180.1 |
| 2010/0301098 A1* | 12/2010 | Kostrzewski | 227/179.1 |
| 2011/0006104 A1 | 1/2011 | Felix | |
| 2011/0046650 A1* | 2/2011 | Bettuchi | 606/153 |
| 2011/0184444 A1* | 7/2011 | D'Agostino et al. | 606/153 |
| 2012/0253367 A1* | 10/2012 | Yamakawa | 606/153 |
| 2012/0273545 A1* | 11/2012 | Mozdzierz | 227/175.1 |
| 2012/0280018 A1* | 11/2012 | Hessler et al. | 227/175.1 |

* cited by examiner

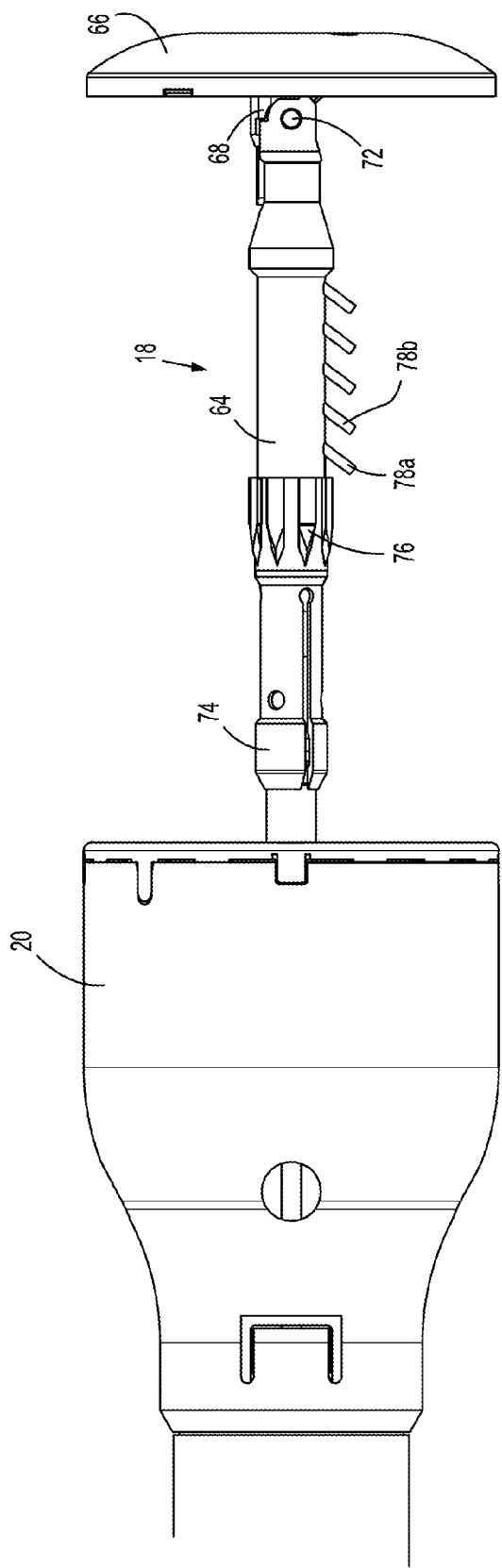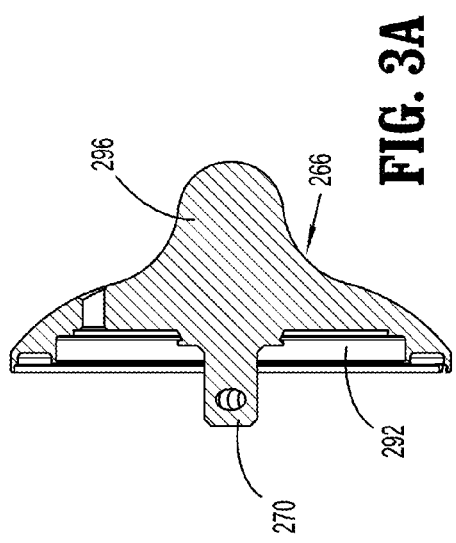

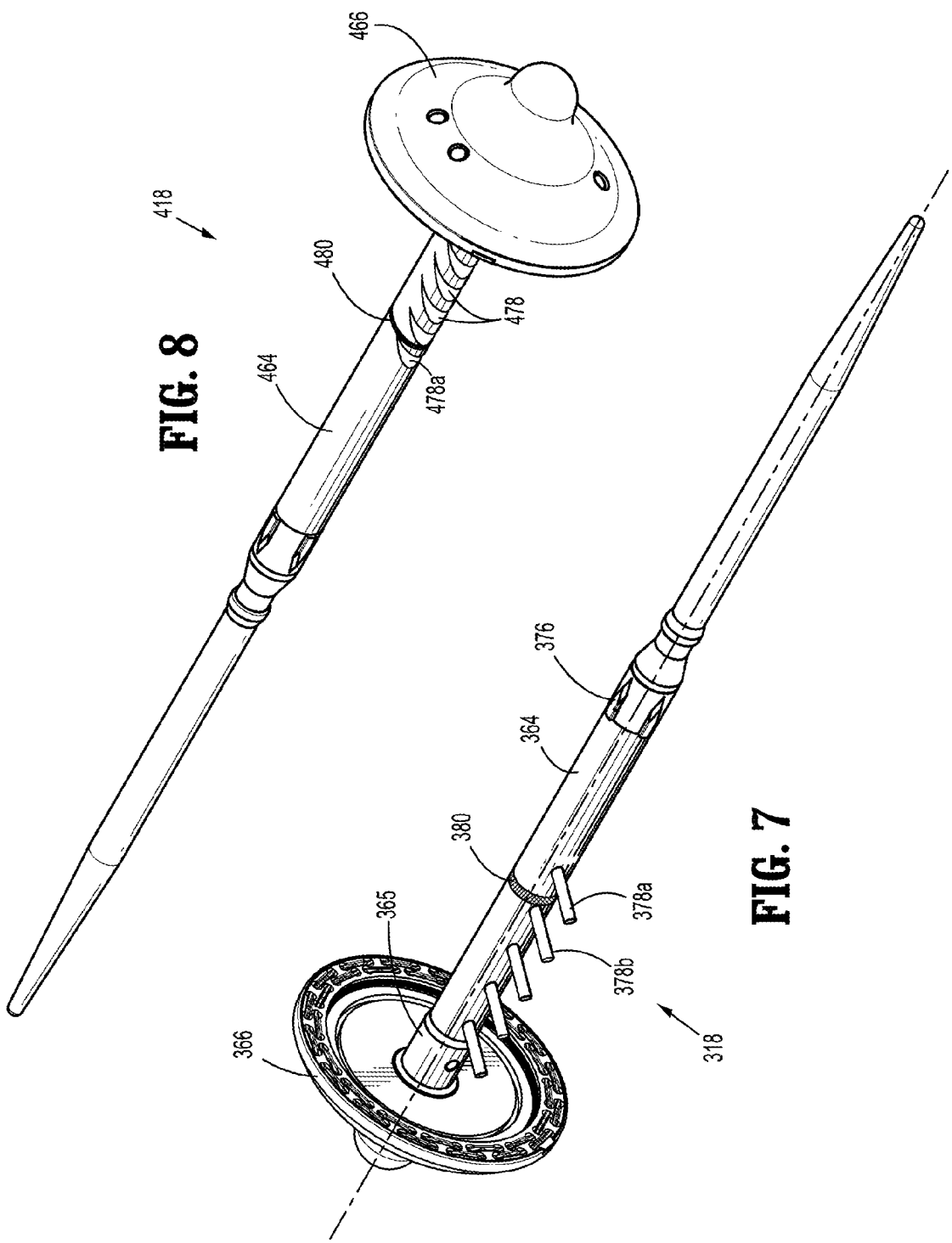

SURGICAL STAPLER

CROSS-REFERENCE TO RELATED APPLICATIONS

This application is a divisional of U.S. patent application Ser. No. 12/637,841, filed Dec. 15, 2009, which claims the benefit of and priority to U.S. Provisional Patent Application Ser. No. 61/142,660, filed Jan. 6, 2009, the entire content of each of the above-identified applications being incorporated in their entireties by reference herein.

BACKGROUND

1. Technical Field

The present disclosure relates to a surgical stapling device and more particularly to a surgical stapling device suitable for treatment of internal hemorrhoids.

2. Background of Related Art

Anastomosis is the surgical joining of separate hollow organ sections. In known circular anastomosis procedures, two ends of organ sections are joined by means of a stapling device which drives a circular array of staples through each organ section and simultaneously cores any tissue interior of the driven circular array of staples to free a tubular passage. Examples of such devices are described in U.S. Pat. Nos. 7,234,624, 6,945,444, 6,053,390, 5,588,579, 5,119,983, 4,646,745, 4,576,167, 4,473,077.

Typically the circular stapling device has an elongated shaft having a handle portion at a proximal end and a staple cartridge at a distal end. An anvil assembly including an anvil rod with an attached anvil head is mounted to the distal end of the device. The anvil is approximated to clamp tissue between the staple holding component and the anvil. The clamped tissue is stapled by actuation of the handle portion to drive circular arrays of staples through the tissue and into anvil depressions on the anvil head to form the staples. An annular knife is advanced with the handle actuation to core tissue inboard of the staple array.

Surgical stapling devices for performing circular anastomosis have also been used to treat hemorrhoids in the rectum. Hemorrhoids are masses of tissue in the anus containing enlarged blood vessels. Internal hemorrhoids are inside the anal canal; external hemorrhoids lie outside the anal canal. Hemmorhoidectomy is a surgical procedure in which the hemorrhoids are removed. Stapled hemorrhoidopexy is a surgical procedure in which a stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply, thus causing the hemorrhoids to shrink. This is used for treatment of internal hemorrhoids.

During the use of a circular stapling device for hemorrhoid treatment, the anvil head and the staple holding component of the device are inserted through and into the rectum with the anvil head and the stapling holding component in an open or unapproximated position. Thereafter, a purse string suture is used to pull the internal hemorrhoidal tissue and/or mucosal tissue toward the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

It would be advantageous to provide a device with an option to adjust the amount of tissue for purse stringing to enhance control over the amount of tissue removed.

SUMMARY

The present disclosure provides an anvil assembly comprising an anvil shaft and an anvil bead. The anvil head has anvil depressions for forming surgical staples and is mounted to the anvil shaft. The anvil shaft has a longitudinal axis and first and second spaced apart elongated projections attached to the anvil shaft and extending therefrom, the projections configured and dimensioned to retain a purse string suture.

In a preferred embodiment, the projections are positioned at an acute angle with respect to the longitudinal axis of the anvil shaft, preferably angling away from the anvil head toward a proximal end of the anvil shaft. In one embodiment, the plurality of projections are substantially equidistantly axially spaced. In one embodiment, the projections comprise a plurality of elongated pins.

In another aspect, the present disclosure provides an anvil assembly comprising an anvil shaft and an anvil head, the anvil head having anvil depressions for forming surgical staples. The anvil head is mounted to the anvil shaft. The anvil shaft has a longitudinal axis and first and second spaced apart cutouts formed therein, the cutouts progressively narrowing in width in a direction toward an opposite wall of the anvil shaft and configured and dimensioned to cinch a purse string suture positioned therein.

In one embodiment the cutouts are substantially equidistantly spaced. Preferably, the cutouts curve inwardly and are directed toward a distal end of the anvil shaft such that they form projecting regions angling toward a proximal end of the anvil shaft.

The present disclosure also provides in another aspect a surgical stapler comprising a handle assembly, an elongated body portion extending distally from the handle assembly, and a head portion disposed adjacent a distal end of the elongated body portion, and including an anvil assembly and a shell assembly. The anvil assembly is movable in relation to the shell assembly between spaced and approximated positions and has an anvil head and a plurality of elongated projections for receiving a purse string suture. The projections extend at an angle with respect to a longitudinal axis of the anvil shaft such that longitudinal axis of the projections are angled with respect to the longitudinal axis of the anvil shaft.

In one embodiment, the anvil assembly includes an anvil shaft extending proximally of the anvil head and removably mountable to an anvil retainer of the stapler. In one embodiment, the projection's are integral with the anvil shaft and formed by angled cuts in the anvil shaft, the cuts preferably angling toward a distal end of the anvil shaft. In one embodiment, the cuts have a first dimension and a second dimension closer to a center of the anvil shaft smaller than the first dimension. In this embodiment, the dimension of the cuts can progressively decrease toward the longitudinal axis of the shaft to form cinch regions for the suture. In other embodiments, the projections are attached to the anvil shaft and comprise a plurality of pins substantially equidistantly longitudinally spaced.

BRIEF DESCRIPTION OF THE DRAWINGS

Various embodiments of the present disclosure are described hereinbelow with reference to the drawings, wherein:

FIGS. 2 and 3 are close up perspective and side views, respectively, of the anvil assembly and shell assembly of FIG. 1;

FIG. 3A is a cross-sectional view of an alternate embodiment of the anvil head;

FIG. 7 is a perspective view of the anvil assembly of FIG. 6;

FIG. 8 is a perspective view of an alternate embodiment of the anvil assembly of the present disclosure;

DETAILED DESCRIPTION OF EMBODIMENTS

Figure 1:
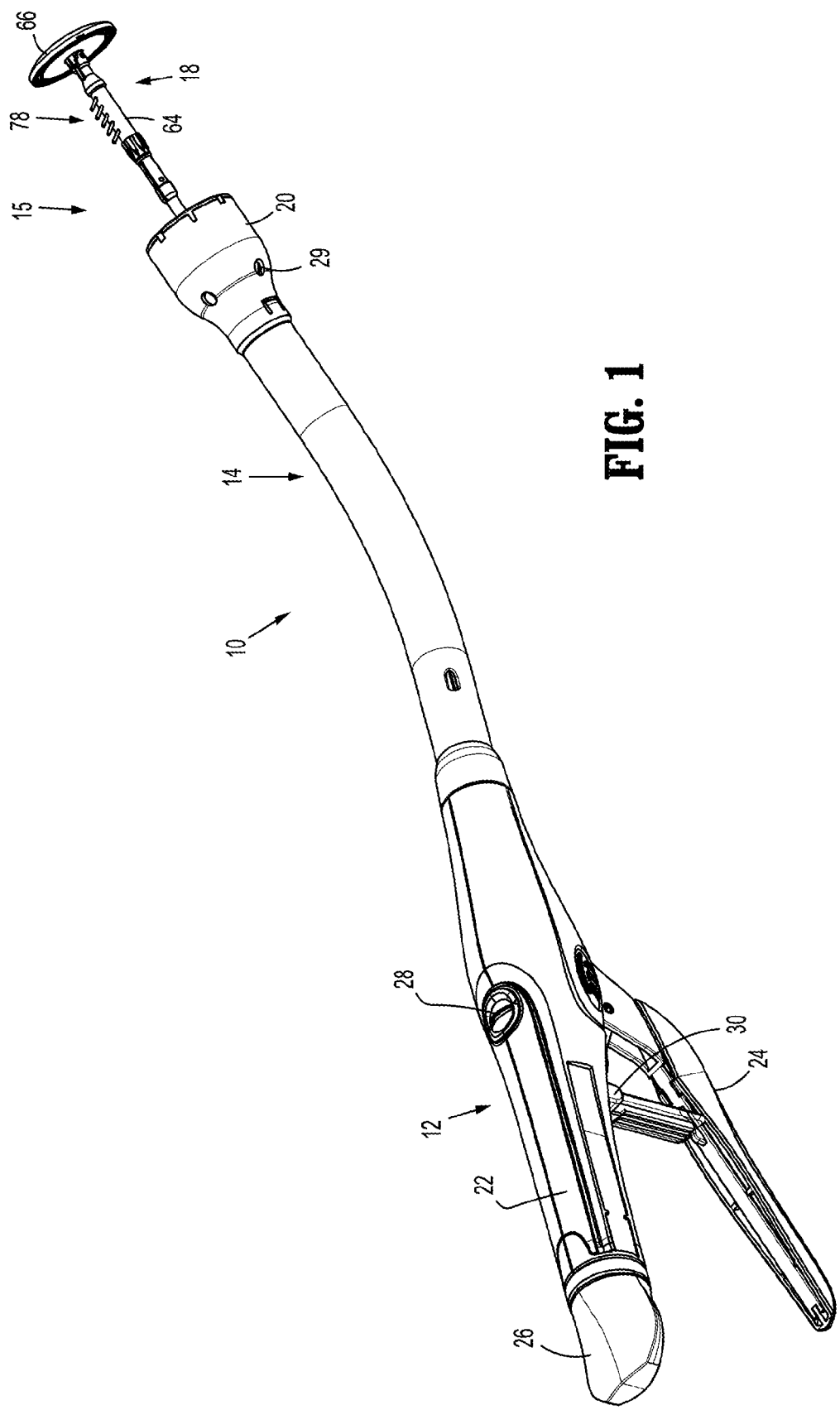
FIG. 1 is a perspective view of a first embodiment of the surgical stapler of the present disclosure.

The presently disclosed surgical stapler will now be described in detail with reference to the drawings in which like reference numerals designate identical or corresponding elements in each of the several views. Throughout this description, the term "proximal" will refer to the portion of the stapler closer to the operator and the term "distal" will refer to the portion of the instrument further from the operator. The presently disclosed stapler is particularly suited for surgical procedures for the treatment of colon prolapse and hemorrhoids, although it can be used for other procedures.

Figure 1A:
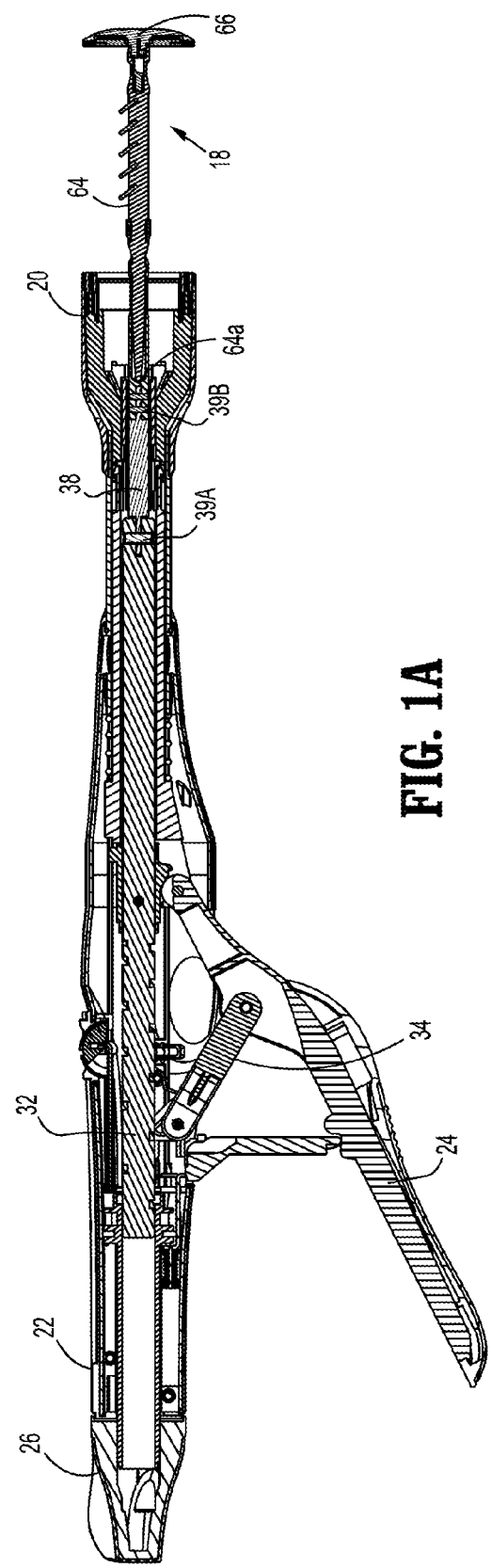
FIG. 1A is a longitudinal cross-sectional view of the surgical stapler of FIG. 1.

FIGS. 1 and 1A illustrate one embodiment of the presently disclosed hemorrhoid stapler 10. Briefly, surgical stapler 10 includes a handle assembly 12, a central body or elongated portion 14 and a distal head portion 15. Head portion 15 includes an anvil assembly 18 and a shell assembly 20. Except where otherwise noted, the components of stapler 10 are generally formed from thermoplastics including polycarbonates, and metals including stainless steel and aluminum. The particular material selected to form a particular component will depend upon the strength requirements of the particular component. For example, the anvil may be formed from a metal such as stainless steel, whereas portions of handle assembly 12 may be formed from thermoplastic such as a polycarbonate. Alternately, other materials having the requisite strength requirements which are suitable for surgical use may be used to form the components of stapler 10.

Handle assembly 12 includes a stationary handle 22, a tiring trigger 24, an approximation knob 26, an indicator assembly 28, and a lockout mechanism 30. Approximation knob 26 functions to retract and advance a drive screw 32 to advance or retract anvil assembly 18 in relation to shell assembly 20. Firing trigger 24 functions to advance a pusher link 34 to actuate a pusher to eject staples from shell assembly 20. Each of the components of handle assembly 12 identified above are substantially as described in U.S. Pat. No. 7,303,106 ("'106 patent") entitled "Surgical Stapling Device With Visual Indicator" which, issued on Dec. 4, 2007. The '306 patent is incorporated herein by reference in its entirety. Accordingly, these components and assemblies will not be described in detail herein.

Figure 1B:
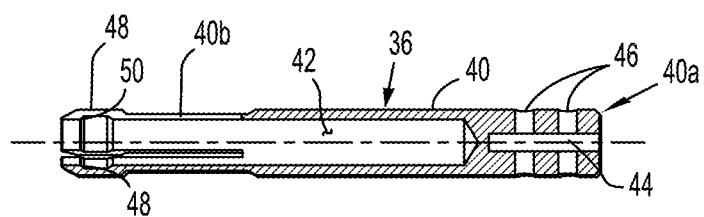
FIG. 1B is a cross-sectional view of the anvil retainer of the stapler of FIG. 1.
Figure 1C:
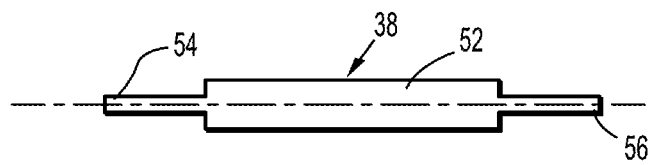
FIG. 1C is a side view of the connector of the stapler of FIG. 1.

Referring to FIGS. 1A-1C, an anvil retainer 36 is secured to a distal end of drive screw 32 by a connector 38. Anvil retainer 36 includes a body 40 defining an elongated bore 42. A proximal end 40a of body 40 includes a longitudinal slot 44 and a pair of transverse throughbores 46. A distal end 40b of body 40 includes three segmented flexible arms 48. Each of the arms 48 has an inner retention surface 50 which will be described in further detail below.

Connector 38 includes a central body 52 having a proximal extension 54 and a distal extension 56. Proximal extension 54 is dimensioned to be received within a slot (not shown) formed in the distal end of drive screw 32. Extension 54 and the distal end of drive screw 32 each define a transverse throughbore for receiving a pin, rivet, screw or the like 39A for fixedly securing connector 38 to drive screw 32. Distal extension 56 is dimensioned to be received within slot 44 of body 40 of anvil retainer 36. Extension 56 includes a pair of spaced throughbores which align with throughbores 46 of anvil retainer 36 and are dimensioned to receive pins, screws, rivets or the like 39B to fixedly secure anvil retainer 36 to connector 38. Although pins, screws, rivets or the like are specifically disclosed for securing connector 38 to drive screw 32 and anvil retainer 36, other known fastening techniques are envisioned, e.g., welding, crimping, and interlocking structure. In an alternate embodiment, the connector and anvil retainer can be replaced with a single part, e.g. an elongated anvil retainer, having an extended length to function similarly to the extended length resulting from the provision of connector 38.

Figure 2:
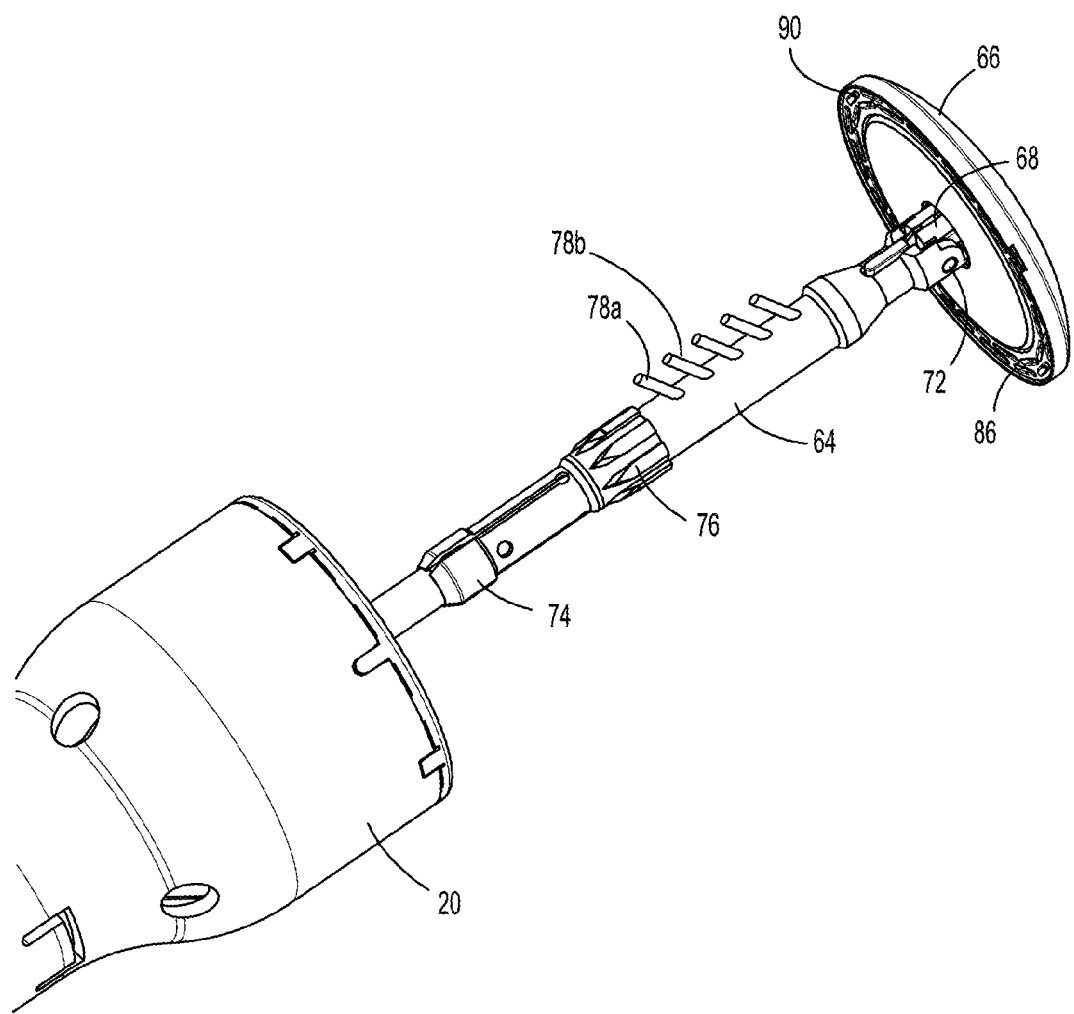

Referring to FIGS. 2 and 3, anvil assembly 18 includes an anvil shaft or center rod 64 and an anvil head 66. Anvil shaft 64 includes a tapered proximal blunt end 64a (FIG. 1A) and an opposite distal end for mounting to anvil post 68 of anvil head 66. A pin 72 (or alternatively a screw, rivet or the like) mounts the anvil post 68 to anvil shaft 64. It should be appreciated, that anvil post 68 can be pivotally mounted to anvil shaft 64 so that the anvil can move between an operative non-lilted position to a tilted position. This is described in detail in U.S. Pat. No. 7,303,106, the entire contents of which are incorporated herein by reference. Alternatively, the anvil can be fixedly (non-pivotably) mounted to the anvil shaft 64. This is shown for example in the embodiment of FIGS. 6 and 7 described below.

Anvil shaft 64 includes a stepped surface or ring 74 which is configured to engage retention surfaces 50 (FIG. 1B) of flexible arms 48 to releasably secure anvil shaft 64 to anvil retainer 36. An orientation groove or grooves is provided in anvil shaft 64 beneath splines 76 to effect proper alignment of splines 76 about shaft 64 to facilitate proper alignment of anvil assembly 18 and shell assembly 20 when anvil assembly 18 is retracted (approximated) towards shell assembly 20.

Anvil shaft 64 can have over-molded splines 76, or alternatively, the anvil shaft can have machined splines.

Anvil shaft 64 has a series of longitudinally spaced projections in the form of pins 78 as shown. The pins 78 provide for a purse-string attachment location. Although the projections are shown in the form of pins, other outwardly extending elongated structure for retaining purse string suture is also contemplated. As shown, five pins are provided, although a fewer or greater number of pins are also contemplated.

The pins 78 extend radially outwardly from the anvil shaft 64 and are positioned at an angle to a longitudinal axis of the anvil shaft. That is, a longitudinal axis of the pins is angled with respect to a longitudinal axis of the anvil shaft 64. In a preferred embodiment, the angle of the pins with respect to the longitudinal axis is between about 30 degrees and about 60 degrees, although other angles are also contemplated as long as they are sufficient to capture the suture. The pins 78 preferably angle toward the proximal end of the anvil shaft 64 to help retain the suture therebetween, but can alternatively be angled in other directions. Also, although shown as straight, the projections can be curved and/or have multiple angles. The pins can be pressed, machined or attached by other techniques to the anvil shaft 64. The projections, e.g. pins, can be formed integrally/monolithically with the anvil shaft or separate components attached to the shaft.

The pins are configured to receive a purse-string suture therebetween, thereby creating a catch or capturing region to retain the suture between two adjacent pins 78. The series of pins 78 enables the user to decide the amount of tissue desired for purse stringing, e.g., placing the suture between the two proximal pins 78a, 78b would enable additional tissue to be taken and presented for stapling compared to distal pins.

It should be appreciated that the suture can also be retained by wrapping around the individual pin or pins 78 instead of placement between two adjacent pins.

Although the pins are shown as substantially identical, the size and configuration of the pins can vary along the length of the anvil shaft 64. Also, although shown substantially equidistantly axially spaced, the distance between adjacent pins can vary.

In the illustrated embodiment, the anvil shaft is of circular cross-section with the pins extending radially from the circumferential surface of the anvil shaft.

Figures 4, 5:
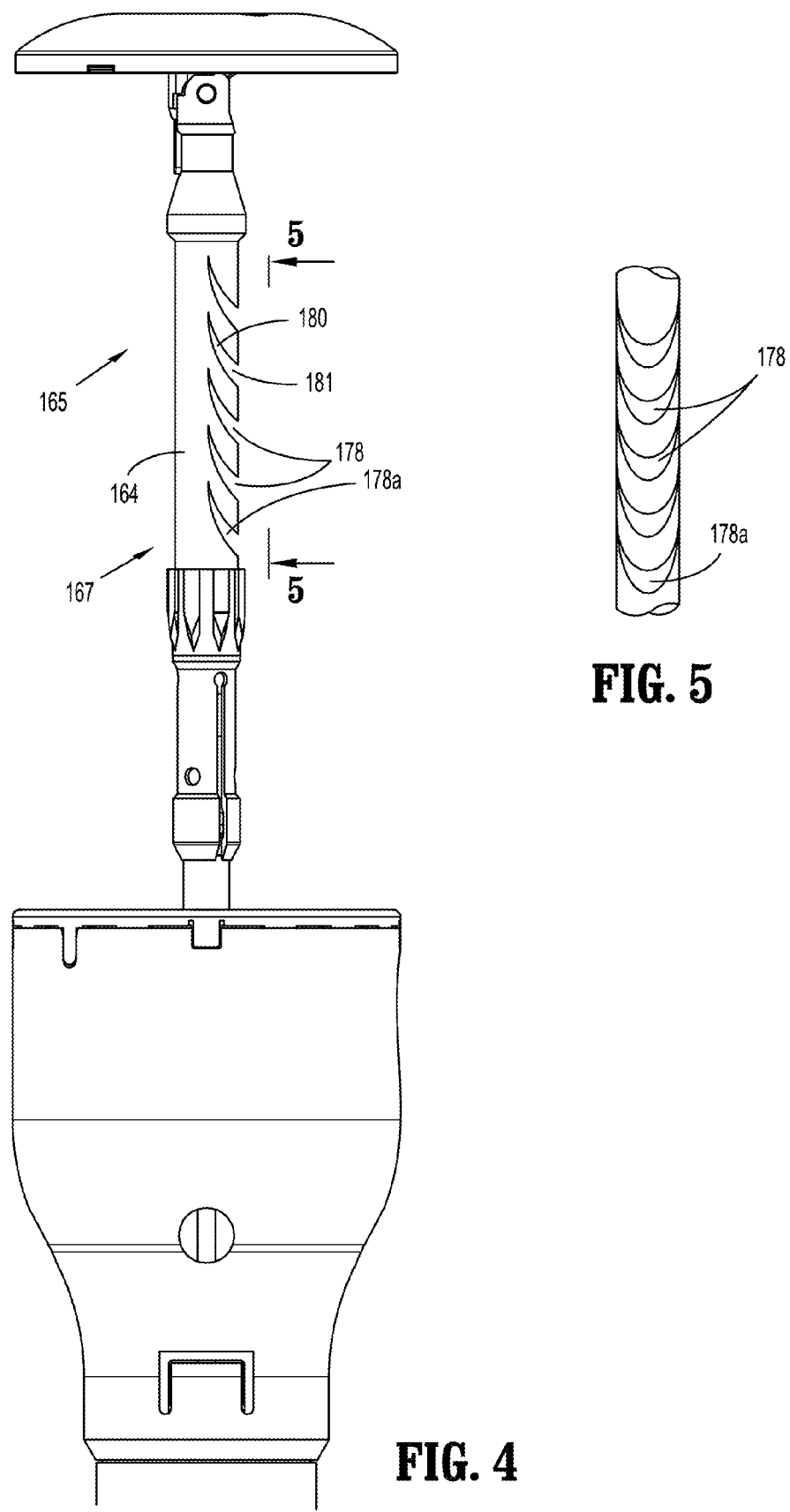
FIG. 4 is a side view of an alternate embodiment of the anvil assembly for use with the surgical stapler of FIG. 1.
FIG. 5 is a top view of a portion of the anvil shaft of FIG. 4.

In the alternate embodiment of FIGS. 4 and 5, a different structure is disclosed for capturing and retaining the purse string suture. Except for the suture retaining structure, the anvil assembly and shell assembly are identical to that described with respect to the embodiment of FIG. 1. The anvil shaft 164 is mown table to the surgical staplers disclosed herein. For brevity, the description of these identical components will not be repeated.

Turning to the structure for receiving the purse string suture of FIGS. 4 and 5, the anvil shaft 164 has a series of cutouts 178 forming cinch spots to grasp the suture. As shown, each of the cutouts 178 is arcuate and cut in a direction toward a distal end 165 of the anvil shaft 164. This angled cut forms a plurality of projecting surfaces or projections extending toward a proximal end 167 of the anvil shaft 164. The cutouts 178 narrow in dimension as they extend toward an opposing wall of the shaft, such that inner region 180 is narrower than outer region 181. The inner regions 180 preferably narrow to a dimension smaller than an outer dimension of the purse string suture so the suture is cinched within the inner region 180 when placed through the cutout 178. As with the pins 78 described above, the user can select the amount of tissue desired by selecting the appropriate cutout 178 in which to cinch the suture, e.g. the more proximal the cutout, the more tissue to be taken and presented for stapling (the proximalmost cutouts 178a providing the most tissue). Although five cutouts are shown, a fewer or greater number of cutouts are also contemplated. The cutouts are also shown as extending to a depth approximately up to the central longitudinal axis of the shaft; cutouts of different depths are also contemplated. Also, although the cutouts as shown are substantially identical, the configuration of the cutouts can vary along the anvil shaft 164. Also, although shown equidistantly axially spaced, the spacing between the cutouts 178 can be varied. The remaining components, e.g. anvil head, are identical to the embodiment of FIG. 1.

As discussed above, anvil retainer 36 (FIG. 1B) defines an elongated bore 42 which is dimensioned to receive anvil shaft 64 such that stepped surface 74 of shaft 64 engages retention surface 50 to releasably secure anvil assembly 18 to anvil retainer 36. In one embodiment, anvil shaft 64 is of a length to protrude from the anus when properly positioned during a surgical procedure to treat colon prolapse. By protruding from the anus, the interface between the anvil shaft 64 and anvil retainer 36 is exposed and visible for attachment. For example, in one embodiment, shaft 64 extends outwardly from a face 86 (FIG. 2) of anvil head 66 a distance greater than about three inches, and for example extends outwardly from face 86 of anvil head 66 a distance of about 3.55 inches. In another embodiment, the shaft extends outwardly a distance of greater than about five inches, and for example extends about 5.234 inches.

Anvil head 66 is shown with a low distal profile, however, other shapes are contemplated such as the bulbous, smoothly contoured anvil 266 illustrated in FIG. 3A. Bulbous portion 296 facilitates insertion of head 266 through a purse string suture. The anvil head 266 can be attached to the anvil shafts disclosed herein. Cutting ring 292 is shown attached to anvil head 266.

Figure 6:
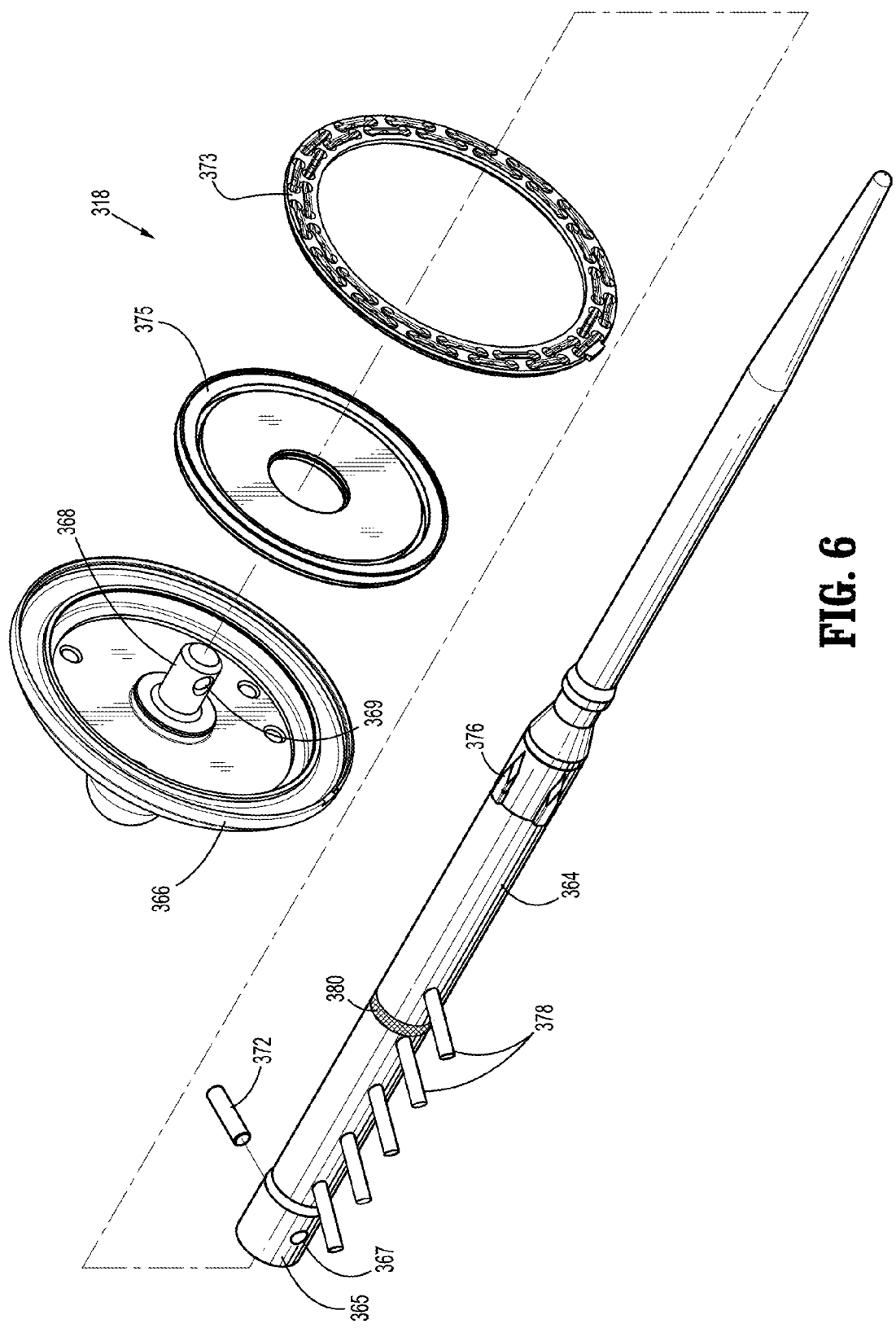
FIG. 6 is an exploded view of an alternate embodiment of the anvil assembly of the present disclosure.

The bulbous anvil head can be used with anvils pivotally attached to an anvil shaft via anvil post 270. Alternatively, the bulbous anvil head can be non-pivotably attached to the anvil shaft such as anvil head 366, 466, shown in FIGS. 7 and 8, respectively. In the embodiment of FIGS. 6 and 7, bulbous anvil head 366 has an anvil post 368 which receives proximal end 365 of anvil shaft or center rod 364 thereover. A pin 372 (or other fastening or attachment structure) extends though opening 367 and 369 of anvil shaft 364 and anvil post 368, respectively, to fixedly (non-pivotably) secure the anvil shaft 364 to anvil head assembly 366. Anvil 373 containing annular rows of anvil depressions is secured to anvil head 366. Cutting ring 375 is positioned in a recess of anvil 373. In all other respects, the anvil assembly 318 is identical to the anvil assembly of FIG. 1 and has e.g. angled projections 378 for reception of purse string sutures, splines 376, etc. A marking ring 380 adjacent the proximalmost suture receiving structure can also be provided as shown in the embodiment of FIG. 6, as well as in the other embodiments disclosed herein, to indicate to the user that a proximalmost pin or cutout is being utilized which present the largest amount of tissue for stapling.

A bulbous anvil head can also be used in a non-pivoting anvil assembly such as illustrated in FIG. 8. The anvil assembly 418 of FIG. 8 is identical to the anvil assembly 165 of FIG. 4, except that the anvil head is non-pivotally attached to anvil shaft 464, a bulbous head 466 is provided, and a marking ring 480 is provided on anvil shaft 464 adjacent the proximalmost cutout 478a of the series of cutouts 478 forming projections.

It should be appreciated that the anvil heads of the embodiments of FIGS. 1 and 4, respectively, can be used with anvil assemblies wherein the anvil heads non-pivotably mounted to the anvil shafts, such as the embodiments of FIGS. 7 and 8.

Figure 1D:
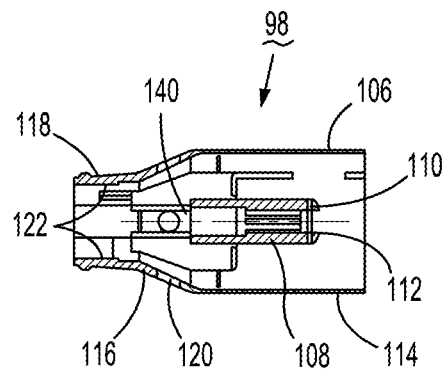
FIGS. 1D and 1E are cross-sectional views of portions of the shell assembly of FIG. 1.
Figure 1E:
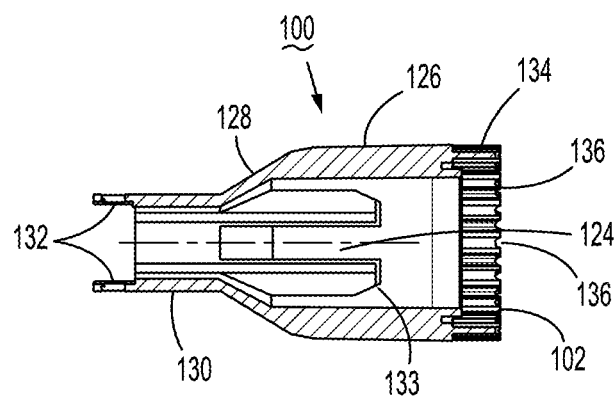

Referring to FIGS. 1A, 1D and 1E, shell assembly 20 is secured to the distal end of central body portion 14 in a manner substantially similar to that described in the '106 patent incorporated herein by reference. Shell assembly 20 includes a shell or housing 98, a pusher back 100, a cylindrical knife 102, and a staple guide housing one or more rows of staples (not shown). Vent holes 29 (FIG. 1) are provided in shell assembly 20.

Shell 98 includes an outer housing portion 106 and an inner guide portion 108 having grooves 110 for mating with splines 76 on anvil shaft 64. Outer housing portion 106 defines a throughbore 112 having a distal cylindrical section 114, a central conical section 116 and a proximal smaller diameter cylindrical section 118. A plurality of openings 120 are formed in conical section 116. Openings 116 are dimensioned to permit fluid and tissue passage during operation of stapler 10. A pair of diametrically opposed flexible engagement members 122 are formed on proximal cylindrical section 118 of shell 98. Engagement members 122 are positioned to be received in openings formed on a distal end of body portion 14 to secure shell 98 to body portion 14.

Pusher back 100 includes a central throughbore 124 which is slidably positioned about inner guide portion 108 of shell 98. Pusher back 100 includes a distal cylindrical section 126 which is slidably positioned within distal cylindrical section 114 of shell 98, a central conical section 128 and a proximal smaller diameter cylindrical section 130. The proximal end of pusher back 100 includes members 132 which are configured to lockingly engage with a pusher link of stapler 10 as described in the '106 patent incorporated by reference herein. Pusher back 100 also defines a receptacle 133 for receiving excised tissue. Receptacle 133 is preferably configured to have a depth of substantially within the range of approximately 0.275 cm (approximately 0.75 inches) to approximately 0.79 cm (approximately 2.0 inches). For example, in one embodiment, the receptacle 215 is configured to define a depth of approximately 0.52 cm (approximately 1.33 inches)

The distal end of pusher back 100 includes a pusher 134. Pusher 134 includes a multiplicity of distally extending fingers 136 dimensioned to be slidably received within slots (not shown) formed in staple guide 104 to eject staples (not shown) therefrom. Cylindrical knife 102 is retained within the central throughbore of pusher back 100 to fixedly secure knife 102 in relation to pusher 134. Knife 102 may be retained within pusher back 100 using adhesives, crimping, pins, friction, etc. The distal end of knife 102 includes a circular cutting edge.

The rigid bushing 140 is supported in the proximal end of inner guide portion 108 of shell 98. Bushing 140 defines a throughbore dimensioned to slidably receive anvil retainer 36 and anvil shaft 64 of anvil assembly 18. Bushing 140 provides lateral support for flexible arms 48 of anvil retainer 36 when the anvil assembly 18 has been approximated to prevent disengagement of anvil assembly 18 from anvil retainer 36. In the unapproximated position, flexible arms 48 are positioned externally of bushing 140 to permit flexing of the arms for removal of anvil assembly 18 front retainer 36.

Figure 9:
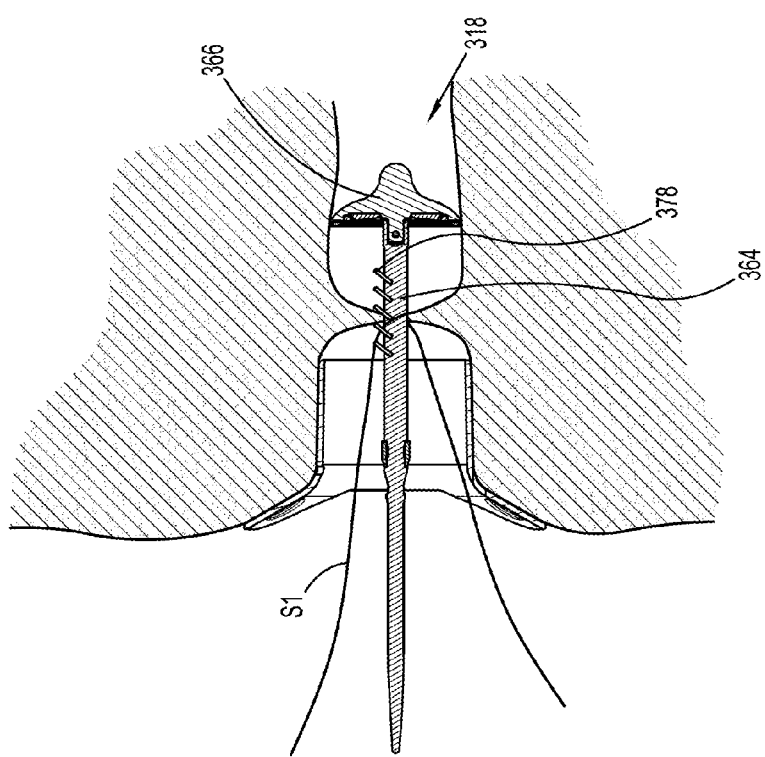
FIG. 9 is a side view illustrating placement of the purse string suture in an anvil assembly of the present disclosure.

As discussed above, stapler 10 is particularly suitable for use in surgical procedures for treating colon prolapse. During such procedure, an access port can be inserted into the anus to facilitate access to the prolapsed colon. Next, a purse string suture S1 is placed into, above or in the vicinity of the colon prolapse and the anvil assembly 318 is inserted through the access port into the anus and rectum. Thereafter, the purse string suture S1 is placed between (or alternately wrapped around) selected adjacent pins 378 (or pins 78) as shown in FIG. 9. Pins 378 are longitudinally spaced along shaft 364 such that the amount of tissue drawn into the shell assembly can be controlled by properly selecting the two pins 378 (or 78) to which the purse string suture is inserted between. A greater amount of tissue will be drawn into shell assembly by capturing and retaining the purse string suture between the two proximalmost pins 378a, 378b. The suture ends are tightened and pulled toward the user, therefore pulling the tissue proximally. The surgeon can then visualize the tissue to be stapled, i.e. the tissue donut to be removed. The stapling instrument, e.g. instrument 10 of FIG. 1, is inserted through the port and attached to the anvil assembly, with the elongated anvil shaft and elongated instrument shaft providing increased visibility. Anvil assembly 35S and the shell assembly 20 are then approximated via knob 26 to draw the prolapsed colon into shell assembly 20.

When surgical stapler 10 is fully approximated, firing trigger 24 can be actuated or fired in a manner described in the '106 patent to staple, sever and allow removal of a portion of the prolapsed colon. Thereafter, the stapler is at least partially unapproximated and removed from the anus with the excised tissue contained within receptacle 133 of pusher back 100 within shell assembly 20. In the embodiments where a lilting anvil is used, after the firing step and sufficient movement of the anvil away from the shell assembly 20, the anvil will tilt (not shown) to its inoperative position to facilitate removal.

Figure 10:
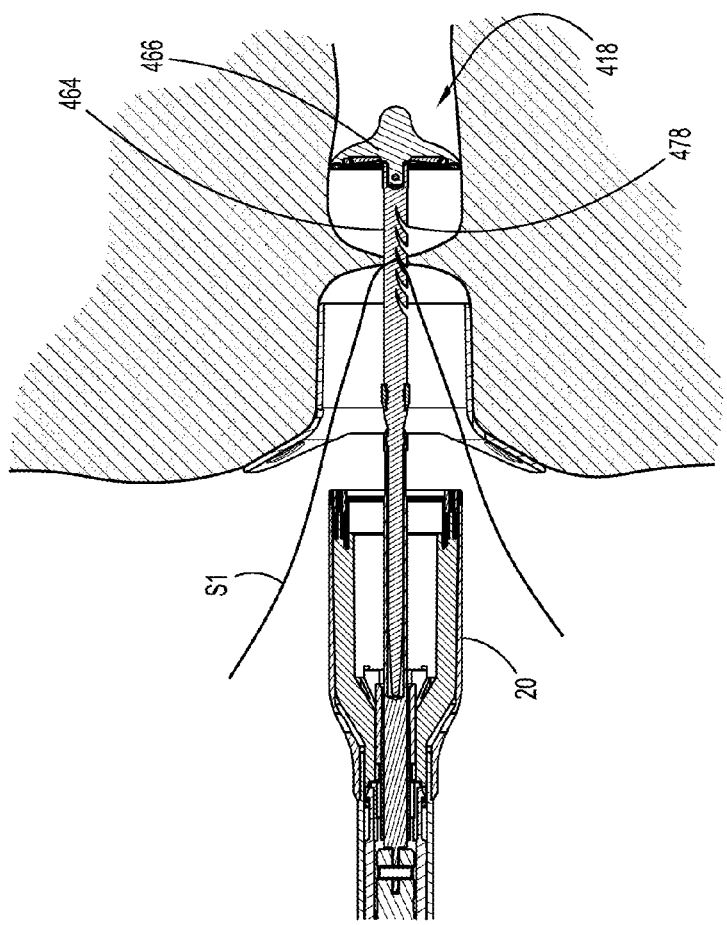
FIG. 10 is a side view illustrating placement of the purse string suture in an anvil assembly of the present disclosure.

FIG. 10 illustrates a purse string suture S1 placed within a cutout 478 of anvil shaft 474 of anvil assembly 418 of FIG. 8. FIG. 10 also illustrates the shell assembly 20 containing the staples with the procedural steps similar to that described above with reference to FIG. 9.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An anvil assembly comprising an anvil shaft and an anvil head, the anvil head having anvil depressions for forming surgical staples, the anvil head mounted to a distal end of the anvil shaft, the anvil shaft having a central longitudinal axis and first and second spaced apart cutouts formed therein, each cutout being defined by a first surface and a second surface, the first and second surfaces of each cutout extending distally from an opening defined by the cutout towards the anvil head, the first and second surfaces of each cutout converging at a point of intersection located distal to the opening so as to define an acute angle therebetween, whereby each cutout progressively narrows in width in a distal direction to cinch a purse string suture positioned therein.

2. The anvil assembly of claim 1, wherein the cutouts curve inwardly toward the central longitudinal axis.

3. The anvil assembly of claim 1, wherein the cutouts are substantially equidistantly spaced.

4. The anvil assembly of claim 1, wherein the cutouts form projecting regions angling toward a proximal end of the anvil shaft.

5. A surgical staple applying apparatus comprising:
a handle assembly;
an elongated body portion extending distally from the handle assembly; and
a head portion disposed adjacent a distal end of the elongated body portion and including an anvil assembly and a shell assembly, the anvil assembly being movable in relation to the shell assembly between spaced and approximated positions, the anvil assembly having an anvil shaft, an anvil head secured to a distal end of the anvil shaft, and a plurality of elongated projections for receiving a purse string suture, the projections extending at an angle with respect to a central longitudinal axis of the anvil shaft, the projections being integral with the anvil shaft and formed by angled cutouts in the anvil shaft, each cutout defining an opening, and angling toward the distal end of the anvil shaft, each cutout being defined by a first surface and a second surface, the first and second surfaces of each cutout extending distally from the opening towards the anvil head and converging at a point of intersection located distal to the opening so as to define an acute angle therebetween.

6. The surgical stapler of claim 5, wherein each cutout defines a first width adjacent the opening thereof, and a second width closer to the central longitudinal axis of the anvil shaft smaller than the first width.

7. The surgical stapler of claim 6, wherein the width of each cutout progressively decreases toward the central longitudinal axis of the anvil shaft to form cinch regions for the suture.

8. An anvil assembly comprising:
 an anvil head including a plurality of depressions configured to form surgical staples; and
 an anvil shaft defining a central longitudinal axis and having proximal and distal ends, the anvil head being positioned adjacent the distal end of the anvil shaft, the anvil shaft including at least one cutout configured to cinch a purse string suture positioned within the at least one cutout, each cutout being defined by a first surface and a second surface, the first and second surfaces of each cutout extending distally from an opening defined by the cutout towards the anvil head, the first and second surfaces of each cutout converging at a point of intersection located distal to the opening so as to define an acute angle therebetween, each cutout defining a width measured along the central longitudinal axis that is narrower at a first location positioned closer to the central longitudinal axis than at a second location positioned further from the central longitudinal axis.

9. The anvil assembly of claim 8, wherein the width of the at least one cutout is progressively narrower in a direction towards the longitudinal axis.

10. The anvil assembly of claim 8, wherein the at least one cutout is curved in configuration.

11. The anvil assembly of claim 10, wherein the at least one cutout curves inwardly towards the central longitudinal axis.

12. The anvil assembly of claim 8, wherein the at least one cutout includes a plurality of cutouts.

13. The anvil assembly of claim 12, wherein the plurality of cutouts are spaced equidistant from each other along the central longitudinal axis.

14. The anvil assembly of claim 12, wherein the plurality of cutouts are identical.

15. The anvil assembly of claim 8, wherein the at least one cutout defines a protection angled towards the proximal end of the anvil shaft.

16. The anvil assembly of claim 8, wherein the at least one cutout includes an inner region and an outer region, the inner region being positioned closer to the central longitudinal axis than the outer region, and wherein the width of the inner region is smaller than the width of the outer region.

17. The anvil assembly of claim 16, wherein the width of the inner region of the at least one cutout is less than a cross-sectional dimension of the purse string suture measured along an axis transverse to a longitudinal axis of the purse string suture.

* * * * *